United States Patent [19]
Bloodsaw

[11] Patent Number: 5,655,543
[45] Date of Patent: Aug. 12, 1997

[54] EAR FASTENER FOR ORAL CONDOMS

[76] Inventor: Paula A. Bloodsaw, 67 Manchester, Apt. D, San Francisco, Calif. 94110

[21] Appl. No.: 694,621

[22] Filed: Aug. 9, 1996

[51] Int. Cl.$^6$ .................................................. A61F 6/02
[52] U.S. Cl. ........................ 128/842; 128/857; 128/859
[58] Field of Search ................................. 128/842, 844, 128/918, 857, 858, 830, 846; 446/27; 2/2, 6.3, 9, 15, 171.3, 171.6, 171.7, 171.8, 181.8, 426, 410, 429, 182.5; 16/228, 250

[56] References Cited

U.S. PATENT DOCUMENTS

| | | | |
|---|---|---|---|
| 2,116,241 | 5/1938 | Heumann | 128/858 |
| 3,241,904 | 3/1966 | Ditto | 16/228 |
| 4,461,549 | 7/1984 | Reese | 16/228 |
| 4,974,605 | 12/1990 | Esqueda | 128/857 |
| 5,320,112 | 6/1994 | Bloodsaw. | |
| 5,409,016 | 4/1995 | Bloodsaw. | |
| 5,473,395 | 12/1995 | Huang | 16/228 |

*Primary Examiner*—Michael A. Brown
*Attorney, Agent, or Firm*—Thomas I. Rozsa; Tony D. Chen

[57] ABSTRACT

An ear fastener used in conjunction with an oral condom which protects the user from contracting sexually transmitted diseases while engaging in cunnilingus and anal sex. The ear fastener facilitates the clamping and releasing of the lateral end of the oral condom. The ear fastener has a front clamping portion, a rear engagement portion for partially engaging over and behind an ear of a user, and a cover hingeably connected to the front portion by a living hinge. The cover 28 can be hingeably opened or closed such that a central protruding pin aligns with and snaps in a central protruding socket provided on the proximal portion for securing and clamping the lateral end of the oral condom.

14 Claims, 1 Drawing Sheet

EAR FASTENER FOR ORAL CONDOMS

BACKGROUND OF THE INVENTION

1. Field of the Invention

The present invention generally relates to the field of fasteners. More particularly, the present invention relates to the field of ear fasteners for protective masks utilized in oral, vaginal and anal sex.

2. Description of the Prior Art

The inventor and applicant of the present invention is also the patentee of U.S. Pat. No. 5,320,112 issued on Jun. 14, 1994 (hereafter "the '112 Patent") and U.S. Pat. No. 5,409,016 issued on Apr. 25, 1995 (hereafter "the '016 Patent"). The inventor is aware of the prior art references which were disclosed in the '112 and '016 Patents. While the patentee's prior art devices function adequately, the patentee has continuously sought to further improve her ear fasteners used in conjunction with an oral condom.

Both the '112 and '016 Patents disclose an oral condom which protects the user from contracting sexually transmitted diseases while engaging in oral, vaginal or anal sex. The oral condom provides a protective mask which is capable of protecting the facial area of a user from undesirable exposure to infection carrying microorganisms. The oral condom has conformed portions for the lips so that the lips can be more easily moved in a natural way and an extended portion for the tongue so the tongue can move in a natural way and not be hindered by the oral condom.

In the '112 Patent, the oral condom is shaped like an oval with two lateral leg portions which are respectively attached to two unique opposite ear attachments. In the '016 Patent, the oral condom is a unitary piece integrally formed with the ear attachments. The patentee has discovered that using the ear attachments disclosed in the '112 Patent is a very time consuming process and cuts down on the "spontaneity" of the sexual act that they wish to enjoy.

There is always a need to improve the ear attachments for protective masks, so that a user engaging in oral, vaginal and anal sex will be protected from communicable diseases. The improved ear fasteners facilitate the use of the oral condom, where the clamp means on the ear fasteners are easy to use. Therefore, it is desirable to have an improved ear fastener, where the clamp means can be securely fastened to the end of the oral condom and quickly released.

SUMMARY OF THE INVENTION

The present invention is an ear fastener used in conjunction with an oral condom which protects the user from contracting sexually transmitted diseases while engaging in cunnilingus and anal sex. The ear fasteners facilitate the clamping and releasing of the lateral ends of the oral condom.

It is therefore an object of the present invention to provide ear fasteners which are used in conjunction with an oral condom to facilitate the clamping and releasing of the oral condom.

It is an additional object of the present invention to provide ear fasteners which are used in conjunction with an oral condom, so that the tension on the oral condom against the face of a user can easily be adjusted.

It is a further object of the present invention to provide ear fasteners which are efficient and easy to use with an oral condom which is disposable after use, and used for spontaneous use, with the ear fasteners easily and removably clamped to the oral condom so that the ear fasteners can be reused with another oral condom.

It is still a further object of the present invention to provide ear fasteners used in conjunction with an oral condom, so that the oral condom can provide protection to a user from sexually transmitted diseases while engaging in oral, vaginal and anal sex.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DESCRIPTION OF THE PREFERRED EMBODIMENT

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 1:
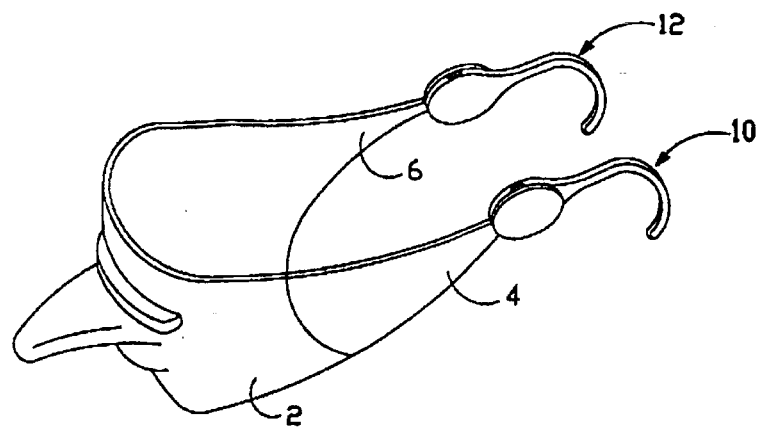
FIG. 1 is an illustrative view of the present invention quick release and clamping ear fastener, showing the ear fasteners clamped to the lateral ends of the oral condom.

Referring to FIG. 1, there is illustrated the present invention quick release and clamping ear fasteners 10 and 12 which are used in conjunction with a conventional oral condom or protective mask 2. The ear fasteners 10 and 12 are utilized with the oral condom 2, so that the condom 2 can be secured to the face of a user and the amount of tension on the oral condom 2 against the face of the user can be easily adjusted. The oral condom 2 has two opposite lateral ends 4 and 6 which are respectively clamped by the ear fasteners 10 and 12 for preventing sexually transmitted diseases when engaging in oral, vaginal or anal sex. The present invention ear fasteners 10 and 12 facilitate the wearing of the oral condom 2. The oral condom 2 used with the present invention is the same device disclosed in the '112 Patent, and the description thereof will not be repeated. It is emphasized that any type of protective masks which have lateral ends may be used with the present invention ear fasteners 10 and 12.

Figure 2:
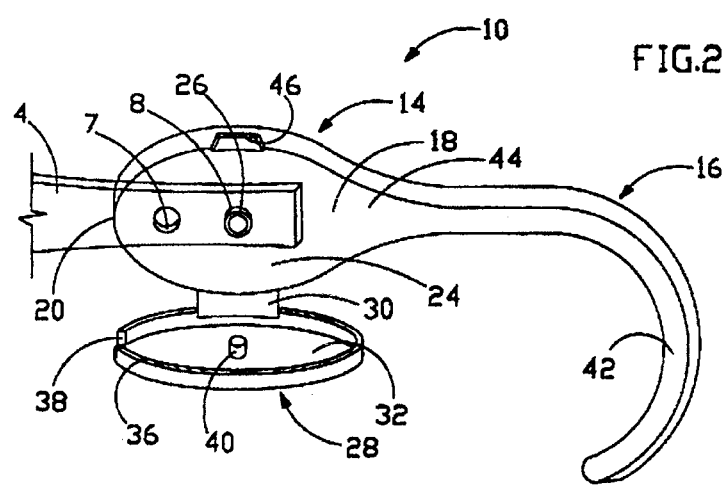
FIG. 2 is an enlarged perspective of the present invention left ear fastener in its unclamped condition.
Figure 3:
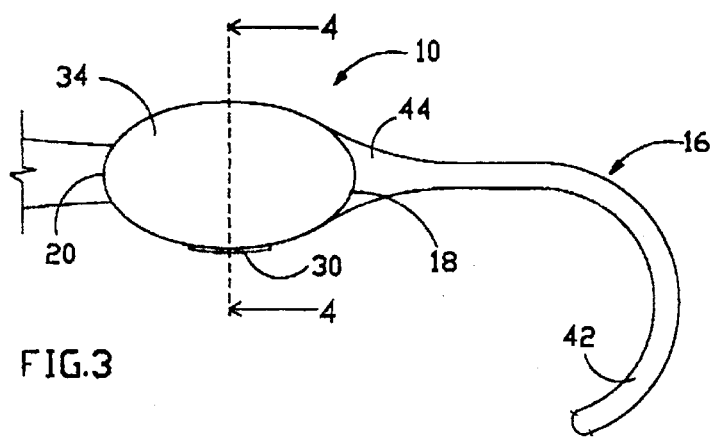
FIG. 3 is an enlarged side elevational view of the present invention left ear fastener in its clamped condition.

Since both ear fasteners 10 and 12 are preferably mirror images, reference will be made to only one ear fastener 10 herein. Referring to FIGS. 2 and 3, there are shown a perspective view of the left ear fastener 10 in its unclamped condition with the lateral end 4 of the oral condom 2 located thereto, and a side elevational view of the ear fastener 10 in its clamped condition, respectively. The ear fastener 10 is reusable after oral, vaginal or anal sex. The ear fastener 10 has an oval-shaped front clamping portion 14 and a rear engagement portion 16. The front clamping portion 14 has a proximal end 18, a distal end 20, an interior side 22 which abuts against the face of a user (see FIG. 4), an exterior side 24, and a central protruding socket 26 which extends slightly out from the exterior surface 24.

An oval-shaped cover 28 is provided with the ear fastener 10 and is substantially the same size as the front clamping portion 14 for completely covering the exterior side 24 of the front portion 14. The cover 28 is hingeably connected at the bottom of the front portion 14 by a living hinge 30. The cover 28 has an interior side 32, an exterior side 34, a protruding periphery rim 36 surrounding the interior side 32 except for one location 38 which is remote from the rear engagement portion 16 that is left open to form an entrance 38, and a central complementary protruding pin 40 which extends out from the interior side 32. The interior side 32 of the cover 28 is located adjacent and parallel to the exterior side 24 of the front portion 14 when the cover 28 is in its clamped condition.

The rear engagement portion 16 has a narrow curved distal end 42 for partially engaging over and behind an ear of a user and a wide proximal end 44 which is integrally formed with the proximal end 18 of the front portion 14, where the thickness of the rear engagement portion 16 is approximately the same thickness as the front portion 14.

Figure 4:
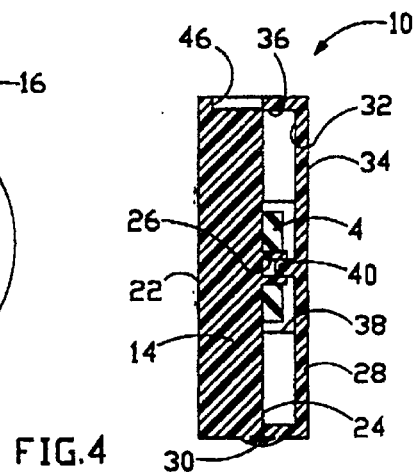
FIG. 4 is a cross-sectional view of taken along line 4—4 of FIG. 3.

Referring to FIG. 4, there is shown a cross-sectional view of the front clamping portion 14 and the cover 28. The cover 28 can be hingeably opened or closed in a vertical direction such that the complementary protruding pin 40 aligns with and snaps in the central protruding socket 26 provided on the front clamping portion 14 for securing and clamping the lateral end 4 of the oral condom, where the lateral end enters from the entrance 38 of the cover 28. A recess 46 is provided at the top of the front clamping portion 14 for facilitating the opening of the cover 28.

It will be appreciated that the cover 28 may be also hingeably connected to the top of the front clamping portion 14, where the cover 28 is opened or closed in the same manner as described above. It will also be appreciated that the cover 28 may be hingeably connected to the proximal end 18 or the distal end 20 of the front clamping portion 14.

Referring to FIG. 1, the tension on the oral condom 2 can be adjusted by adjusting where the lateral ends 4 and 6 are clamped by the ear fasteners 10 and 12 respectively. The oral condom 2 can be adjusted to any particular user because of the unique clamping means of the ear fasteners 10 and 12. The ear fasteners 10 and 12 are partially hooked over and behind the ears of the user and held in place, similar to wearing eyeglasses. Once the oral condom has been used, the ear fasteners 10 and 12 can be detached from the oral condom to be reused with another oral condom.

It will be appreciated that the oral condom 2 illustrated in FIG. 2 has at least two apertures 7 and 8 provided therein as illustrated in FIG. 2, wherein one of the two apertures can be looped to the central protruding socket 26 of the front portion 14 for providing a constant positioning means for the ear fasteners to clamp the oral condom. However, the present invention ear fasteners 10 and 12 do not require these apertures on the oral condom.

The present invention conforms to conventional forms of manufacture or any other conventional way known to one skilled in the art, and is of simple construction and is easy to use. The ear fasteners 10 and 12 can be made from several materials. By way of example, the ear fasteners may be made of plastic material or any suitable material.

It will be appreciated that the front portion 14 of the ear fastener 10 is not limited to the oval shape described above. It is emphasized that while the oval shaped front portion is illustrated, it is also within the spirit and scope of the present invention to utilize many other shape suitable for the front portion of the ear fastener 10, where the cover 28 will also be shaped the same.

Defined in detail, the present invention is a pair of ear fasteners used in conjunction with an oral condom having two opposite ends where a respective ear fastener respectively clamps one respective end of the oral condom, each ear fastener comprising: (a) a rear engagement portion having a narrow curved distal end for partially engaging over and behind an ear of a user and a wide proximal end; (b) an oval-shaped front clamping portion having a distal end, a proximal end integrally formed with the wide proximal end of the rear engagement portion, an exterior side, an interior side, and a central protruding socket extending slightly out from the exterior side, the thickness of the front clamping portion being approximately the same thickness as the rear engagement portion; and (c) an oval-shaped cover being substantially the same size as the front clamping portion for completely covering the exterior side of the front portion, the cover hingeably connected to the front portion by a living hinge and having an exterior side, an interior side, a protruding periphery rim surrounding the interior side except for one location remote from the rear engagement portion which is left open to form an entrance, and a central protruding pin extending out from the interior side, the cover hingeably opened or closed in a vertical direction such that the central protruding pin aligns with and snaps in the central protruding socket of the front clamping portion for securing and clamping an end of the oral condom entering from the entrance; (d) whereby the ear fastener clamps a respective one end of the oral condom for facilitating the wearing of the oral condom.

Defined broadly, the present invention is a pair of ear fasteners used in conjunction with an oral condom having two opposite ends where a respective ear fastener respectively clamps one respective end of the oral condom, each ear fastener comprising: (a) a rear engagement portion having a narrow curved distal end for partially engaging over and behind an ear of a user and a wide proximal end; (b) a front clamping portion having a distal end, a proximal end integrally formed with the wide proximal end of the rear engagement portion, an exterior side, an interior side, and a first mating means extending slightly out from the exterior side, the thickness of the front clamping portion being approximately the same thickness as the rear engagement portion; and (c) a cover being substantially the same size and shape as the front clamping portion for completely covering the exterior side of the front portion, the cover hingeably connected to the front portion by a living hinge and having an exterior side, an interior side, a protruding periphery rim surrounding the interior side except for one location remote from the rear engagement portion which is left open to form an entrance, and a second mating means aligned with the first mating means and extending out from the interior side, the cover hingeably opened or closed such that the two mating means clamp together when the cover is closed and thereby secure an end of the oral condom entering from the entrance.

Defined more broadly, the present invention is a pair of ear fasteners used in conjunction with a protective mask having two opposite ends where a respective ear fastener respectively clamps one respective end of the protective mask, the ear fastener comprising: (a) a rear engagement portion having a distal end for partially engaging over and behind an ear of a user, and a proximal end; (b) a front clamping portion having a distal end, a proximal end integrally formed with the proximal end of the rear engagement portion, a side, and a protruding socket extending out from the side; and (c) a cover being substantially the same size as the front clamping portion and hingeably connected to the front portion, the cover having a side, a protruding periphery rim surrounding the side except for one location remote from the rear engagement portion which is left open to form an entrance, and a complementary protruding pin extending out from the side, the cover hingeably opened or closed such that the protruding pin aligns with and snaps in the protruding socket of the front clamping portion for securing and clamping an end of the protective mask entering from the entrance; (d) whereby the ear fastener clamps the ends of the protective mask respectively for facilitating the wearing of the protective mask.

Defined even more broadly, the present invention is a pair of ear fasteners used in conjunction with a protective mask having two opposite ends where a respective ear fastener respectively clamps one respective end of the protective mask, the ear fastener comprising: (a) a rear engagement portion having a distal end for partially engaging over and behind an ear of a user, and a proximal end; (b) a front clamping portion having a distal end, a proximal end integrally formed with the proximal end of the rear engagement portion, a side, and a first mating means extending out from the side; and (c) a cover being substantially the same size as the front clamping portion and hingeably connected to the front portion, the cover having a side, a protruding periphery rim surrounding the side except for one location remote from the rear engagement portion which is left open to form an entrance, and a second mating means aligned with the first mating means and extending out from the side, the cover hingeably opened or closed such that the two mating means clamp together when the cover is closed and thereby secure an end of the protective mask entering from the entrance.

Defined further even more broadly, the present invention is a fastener used in conjunction with a protective mask, comprising: (a) an engagement portion having a distal end for partially engaging over and behind an ear of a user, and a proximal end; (b) a clamping portion having a distal end and a proximal end connected to the proximal end of the engagement portion; and (c) a cover hingeably connected to the clamping portion and having means for clamping the protective mask; (d) whereby the fastener clamps the protective mask for facilitating the wearing of the protective mask.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to show all of the various forms or modifications in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of patent monopoly to be granted.

What is claimed is:

1. A pair of ear fasteners used in conjunction with an oral condom having two opposite ends where a respective ear fastener respectively clamps one respective end of the oral condom, each ear fastener comprising:

a. a rear engagement portion having a narrow curved distal end for partially engaging over and behind an ear of a user and a wide proximal end;

b. an oval-shaped front clamping portion having a distal end, a proximal end integrally formed with said wide proximal end of said rear engagement portion, an exterior side, an interior side, and a central protruding socket extending slightly out from the exterior side, the thickness of the front clamping portion being approximately the same thickness as said rear engagement portion; and c. an oval-shaped cover being substantially the same size as said front clamping portion for completely covering said exterior side of said front portion, the cover hingeably connected to said front portion by a living hinge and having an exterior side, an interior side, a protruding periphery rim surrounding the interior side except for one location remote from said rear engagement portion which is left open to form an entrance, and a central protruding pin extending out from the interior side, the cover hingeably opened or closed in a vertical direction such that the central protruding pin aligns with and snaps in said central protruding socket of said front clamping portion for securing and clamping an end of said oral condom entering from the entrance;

d. whereby said ear fastener clamps a respective one end of said oral condom for facilitating the wearing of said oral condom.

2. The invention in accordance with claim 1 wherein each ear fastener further comprises a recess for facilitating the opening of said cover.

3. The invention in accordance with claim 1 wherein each said front clamping and rear engagement portions are made of plastic material.

4. A pair of ear fasteners used in conjunction with an oral condom having two opposite ends where a respective ear fastener respectively clamps one respective end of the oral condom, each ear fastener comprising:

a. a rear engagement portion having a narrow curved distal end for partially engaging over and behind an ear of a user and a wide proximal end;

b. a front clamping portion having a distal end, a proximal end integrally formed with said wide proximal end of said rear engagement portion, an exterior side, an interior side, and a first mating means extending slightly out from the exterior side, the thickness of the front clamping portion being approximately the same thickness as said rear engagement portion; and c. a cover being substantially the same size and shape as said front clamping portion for completely covering said exterior side of said front portion, the cover hingeably connected to said front portion by a living hinge and having an exterior side, an interior side, a protruding periphery rim surrounding the interior side except for one location remote from said rear engagement portion which is left open to form an entrance, and a second mating means aligned with said first mating means and extending out from the interior side, the cover hingeably opened or closed such that the two mating means clamp together when the cover is closed and thereby secure an end of said oral condom entering from the entrance.

5. A pair of ear fasteners used in conjunction with a protective mask having two opposite ends where a respective ear fastener respectively clamps one respective end of the protective mask, the ear fastener comprising:

a. a rear engagement portion having a distal end for partially engaging over and behind an ear of a user, and a proximal end;

b. a front clamping portion having a distal end, a proximal end integrally formed with said proximal end of said rear engagement portion, a side, and a protruding socket extending out from the side; and c. a cover being substantially the same size as said front clamping portion and hingeably connected to said front portion, the cover having a side, a protruding periphery rim surrounding the side except for one location remote from said rear engagement portion which is left open to form an entrance, and a complementary protruding pin extending out from the side, the cover hingeably opened or closed such that the protruding pin aligns with and snaps in said protruding socket of said front clamping portion for securing and clamping an end of said protective mask entering from the entrance;

d. whereby said ear fastener clamps said ends of said protective mask respectively for facilitating the wearing of said protective mask.

6. The invention in accordance with claim 5 wherein each ear fastener further comprises a recess for facilitating the opening of said cover.

7. The invention in accordance with claim 5 wherein each said front clamping and rear engagement portions are made of plastic material.

8. The invention in accordance with claim 5 wherein said cover is hingeably connected to said front portion by a living hinge.

9. A pair of ear fasteners used in conjunction with a protective mask having two opposite ends where a respective ear fastener respectively clamps one respective end of the protective mask, the ear fastener comprising:

a. a rear engagement portion having a distal end for partially engaging over and behind an ear of a user, and a proximal end;

b. a front clamping portion having a distal end, a proximal end integrally formed with said proximal end of said rear engagement portion, a side, and a first mating means extending out from the side; and c. a cover being substantially the same size as said front clamping portion and hingeably connected to said front portion, the cover having a side, a protruding periphery rim surrounding the side except for one location remote from said rear engagement portion which is left open to form an entrance, and a second mating means aligned with said first mating means and extending out from the side, the cover hingeably opened or closed such that the two mating means clamp together when the cover is closed and thereby secure an end of said protective mask entering from the entrance.

10. A fastener used in conjunction with a protective mask, comprising:

a. an engagement portion having a distal end for partially engaging over and behind an ear of a user, and a proximal end;

b. a clamping portion having a distal end and a proximal end connected to said proximal end of said engagement portion; and c. a cover hingeably connected to said clamping portion and having means for clamping said protective mask including a protruding socket located on said clamping portion and a complementary protruding pin located on the cover, where the cover is hingeably opened or closed such that the complementary protruding pin aligns with and snaps in the protruding socket of said clamping portion;

d. whereby said fastener facilitates the wearing of said protective mask.

11. The fastener in accordance with claim 10 further comprising a recess for facilitating the opening of said cover.

12. The fastener in accordance with claim 10 wherein said engagement and clamping portions are made of plastic material.

13. The fastener in accordance with claim 10 wherein said fastener is reusable.

14. The fastener in accordance with claim 10 wherein said cover is hingeably connected to said clamping portion by a living hinge.

* * * * *